(12) United States Patent
Hsieh et al.

(10) Patent No.: US 8,487,771 B2
(45) Date of Patent: Jul. 16, 2013

(54) PERSONAL HEALTH MANAGEMENT DEVICE

(75) Inventors: Jeffrey Hsieh, Dove Canyon, CA (US); Dennis Kwan, San Diego, CA (US); Suresh Singamsetty, Aliso Viejo, CA (US)

(73) Assignee: SilverPlus, Inc., Irvine, CA (US)

( * ) Notice: Subject to any disclaimer, the term of this patent is extended or adjusted under 35 U.S.C. 154(b) by 392 days.

(21) Appl. No.: 12/454,715

(22) Filed: May 21, 2009

(65) Prior Publication Data

US 2010/0295684 A1 Nov. 25, 2010

(51) Int. Cl.
*G08B 23/00* (2006.01)

(52) U.S. Cl.
USPC .................. 340/573.1; 340/539.12; 600/301

(58) Field of Classification Search
USPC .................. 340/573.1, 539.12; 600/300, 301
See application file for complete search history.

(56) References Cited

U.S. PATENT DOCUMENTS

| | | | |
|---|---|---|---|
| 5,872,505 A | 2/1999 | Wicks et al. | |
| 7,044,911 B2 | 5/2006 | Drinan et al. | |
| 7,088,233 B2 | 8/2006 | Menard | |
| 7,185,282 B1 | 2/2007 | Naidoo et al. | |
| 7,400,249 B2 | 7/2008 | Monroe | |
| 7,477,143 B2 | 1/2009 | Albert | |
| 7,477,144 B2 | 1/2009 | Albert | |
| 7,616,110 B2 | 11/2009 | Crump et al. | |
| 2006/0055543 A1 | 3/2006 | Ganesh et al. | |
| 2006/0154642 A1 | 7/2006 | Scannell, Jr. | |
| 2008/0001735 A1 | 1/2008 | Tran | |
| 2008/0117060 A1 | 5/2008 | Cuddihy et al. | |
| 2008/0249376 A1 | 10/2008 | Zaleski | |
| 2009/0040052 A1 | 2/2009 | Cameron et al. | |
| 2009/0058635 A1 | 3/2009 | LaLonde et al. | |
| 2009/0115628 A1* | 5/2009 | Dicks et al. | 340/573.1 |
| 2009/0231124 A1* | 9/2009 | Klabunde et al. | 340/539.12 |

FOREIGN PATENT DOCUMENTS

GB 2 348 726 10/2000

OTHER PUBLICATIONS

Co-Pending, U.S. Appl. No. 12/454,714, filed May 21, 2009, "Integrated Health Management Console," assigned to the same assignees as the present invention.
International Search Report PCT/US2010001450, Jul. 2, 2010, Silverplus, Inc.
US Office Action, dated Mar. 30, 2012, for U.S. Appl. No. 12/454,714 to Jeffrey Hsieh, et al.
US Office Action, dated Dec. 3, 2012, for U.S. Appl. No. 12/454,714 to Jeffrey Hsieh, et al.
US Office Action, dated Sep. 15, 2011, for U.S. Appl. No. 12/454,714 to Jeffrey Hsieh, et al.

* cited by examiner

*Primary Examiner* — Thomas Mullen
(74) *Attorney, Agent, or Firm* — Saile Ackerman LLC; Stephen B. Ackerman; Rosemary L. S. Pike

(57) ABSTRACT

A personal health management device is described. The device is part of a system comprising at least one console, one or more devices in wireless communication with the console wherein the console acts as an intelligent gateway through which the one or more devices may communicate to external data and voice networks, and an alert system wherein an alert is triggered by one or more of a user's action and pre-set alarm criteria and wherein the triggering of an alert causes the console to take an action. The device may be a wearable device or it may be implemented in software and reside on third-party hardware.

38 Claims, 6 Drawing Sheets

PERSONAL HEALTH MANAGEMENT DEVICE

RELATED PATENT APPLICATION

This Patent Application is related to U.S. patent application Ser. No. 12/454,714 filed on May 21, 2009, which is herein incorporated by reference in its entirety.

BACKGROUND OF THE INVENTION (1) Field of the Invention

The invention relates to a personal health management device, and more particularly, a personal health management device that has two-way communication ability.

(2) Description of the Related Art

Current products fall mainly into two categories: personal emergency response systems (PERS), and telehealth. The PERS systems allow users to send an alarm signal to remote caregivers in order to request assistance in an emergency. These normally consist of a mobile device wirelessly connecting to a console, which communicates to caregivers via voice calls over standard analog telephone lines. The telehealth systems are for measurements and monitoring of users' health information, such as their vital signs. These are normally connected to remote caregivers using data over the Internet or just using modems over analog telephone lines.

The disadvantages of these systems arise from the fact that they are separate systems which do not share data with each other. This creates operational difficulties and increases equipment costs. For example, vital sign measurements are taken by individual devices and the uploading of data often requires significant user interactions which is very inconvenient to the users. Another major disadvantage is that their functionalities are strictly limited to the individual applications of PERS and telehealth, although data from telehealth systems are very useful to the PERS and vice versa. For example, in the event of an emergency handled by the PERS, the telehealth data in the form of personal health records (PHR) will be needed by the emergency crew (e.g. blood type). By combining telehealth into PERS, the PHR can be displayed by the PERS equipment, or alternatively, the PERS system may automatically send together with the alert signal a pre-programmed message to the caregivers to enable access to the PHR on the network.

Co-pending U.S. patent application Ser. No. 12/454,714 provides an integrated health management system that combines a personal emergency response system with vital signs measurement systems. Personal alert devices are described in several U.S. Patents. U.S. Pat. No. 7,477,143 to Albert discloses a personal alert pendant that sounds an alarm. A monitor hears the alarm and sends an emergency notification. The monitor also can receive input from medical monitoring devices. U.S. Pat. No. 7,400,249 to Monroe shows a personal alarm that can be worn or carried. Radio frequency receivers provide area coverage. U.S. Patent Application 2008/0001735 to Tran describes a health care monitoring system including a wearable device and motion sensor. U.S. Pat. No. 7,477,144 to Albert shows a bedside sound monitoring unit that will send an alarm if the breathing pattern shows deviation from normal. U.S. Pat. No. 5,872,505 to Wicks et al describes a paging system that sends reminders about treatment or appointments to a patient's pager. U.S. Patent Application 2006/0154642 to Scannell shows a health monitoring system including medication reminders, monitoring, alerts, and a motion sensor at exits. U.S. Patent Application 2009/0040052 to Cameron et al discloses a motion sensor that checks at intervals during a user's active time. An alarm will sound if there is no activity. The user can send an all's well signal. If the all's well signal is not received, a help message is sent over a communications channel. U.K. Patent Application 2,348,726 to Doughty et al teaches using sensors on furniture to monitor activity. In the absence of activity, an alarm call is raised. U.S. Patent Application 2008/0117060 to Cuddithy et al teaches a wearable device that sounds an alert if it detects unusual activity. U.S. Patent Applications 2006/0055543 to Ganeeh et al discloses a monitoring center that uses motion sensors to detect a problem and alerts a caregiver.

SUMMARY OF THE INVENTION

A principal object of the present invention is to provide a cost-effective and easy to use personal health management device.

Another object of the invention is to provide a personal health management device that includes a personal emergency response system and integrates other functions.

Yet another object of the invention is to provide a personal health management device that provides emergency response capabilities and also functions as a gateway to collect and share personal health data.

A further object of the invention is to provide a personal health management device that collects motion data and triggers an alert upon absence of motion of the user.

In accordance with the objects of this invention, a personal health management device is described. The device is part of a system comprising at least one console, one or more devices in wireless communication with the console wherein the console acts as an intelligent gateway through which the one or more devices may communicate to external data and voice networks, and an alert system wherein an alert is triggered by one or more of a user's action and pre-set alarm criteria and wherein the triggering of an alert causes the console to take an action. The device may be a wearable device or it may be implemented in software and reside on third-party hardware.

BRIEF DESCRIPTION OF THE DRAWINGS

In the accompanying drawings forming a material part of this description, there is shown.

DESCRIPTION OF THE PREFERRED EMBODIMENTS

The invention relates to a personal health management device, and more particularly, a personal health management device that has two-way communication ability to support data and real-time media traffic such as voice. In particular the invention relates to the device being implemented as a wearable wrist-watch, and combining multiple functions related to health management including time-keeping, personal emergency alert button, two-way voice communication, in-case-of-emergency (ICE) information, event reminders, motion sensor, and home control activators.

Figure 1:
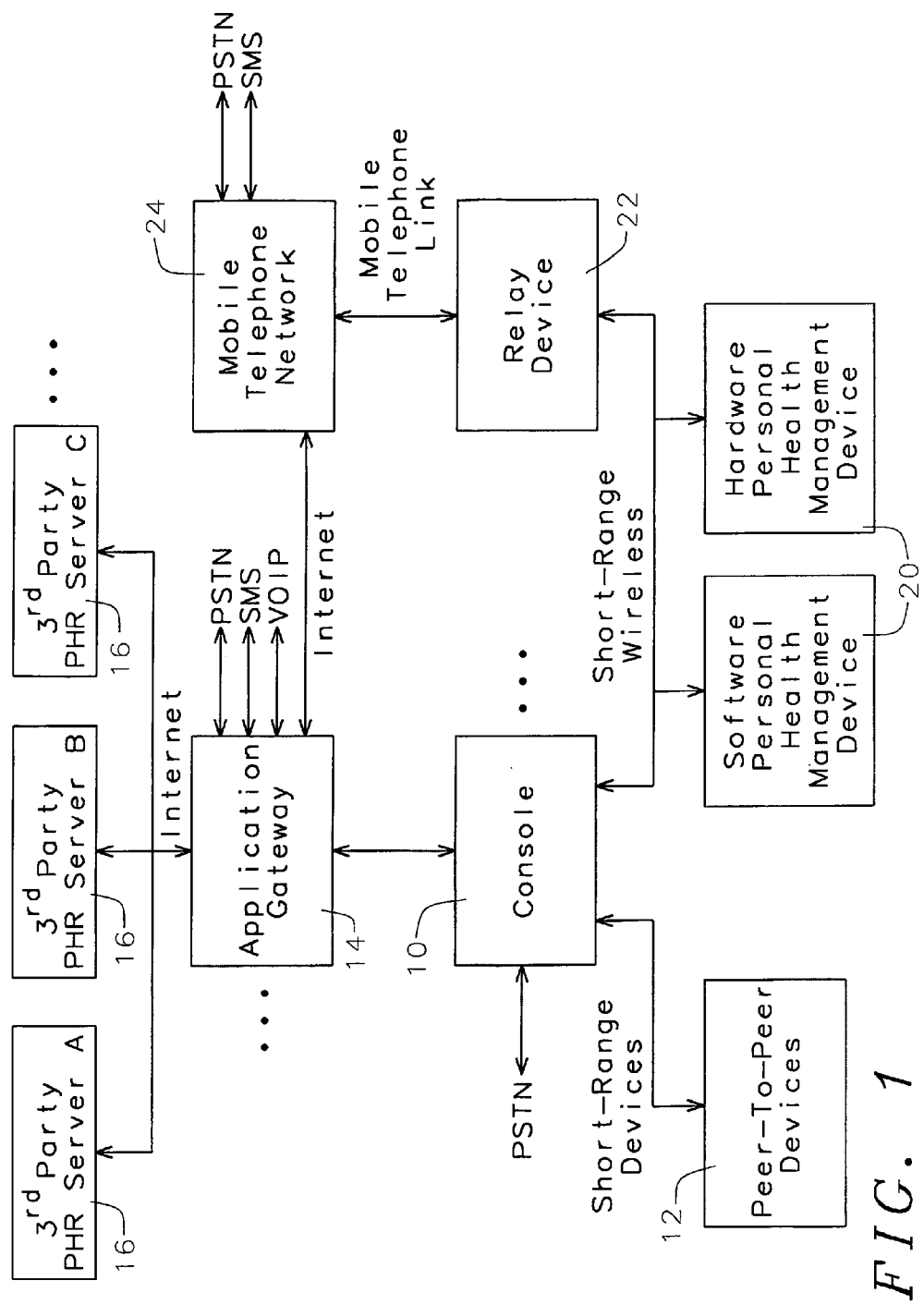
FIG. 1 schematically illustrates an overview of a health management system including the personal health management device of the present invention.

The present invention provides a personal health management device that can be a part of the integrated health management system of co-pending U.S. patent application Ser. No. 12/454,714. This health management system for the home combines a personal emergency response system with vital signs measurement systems. Referring to FIG. 1, the health management system uses one or more consoles 10 to support one or more devices 12 and 20 wirelessly. The Console units may connect to external Application Gateway (AG) units 14 and other communication devices over analog phone lines, internet and wireless data and voice services. The system combines the collection of health data such as vital-sign measurements (sometimes known as telehealth measurements) from the user with communication through the console to external Application Gateways (AG). Third party consolidated service providers 16 can be connected to the system through the Application Gateway which acts as an intelligent conduit between the console and the third-party servers. The AG performs necessary protocol conversion between the console and the third party servers and also consolidates real-time data from the console (e.g. motion data) to summarize results meaningful for storage as personal health records (PHR). The AG also can update any related information from PHR to the consoles (e.g. caregivers' contact info) as needed. Examples of third party servers are: Google Health and Microsoft Healthvault. These servers provide the means to store, organize, and share health information.

The personal health management device of the present invention (hereinafter called Device) 20 is in short-range wireless communication with the console 10 and with other peer-to-peer devices 12. The Device incorporates a radio for communicating wirelessly with Console units as well as other peer-to-peer devices such as home control activators. To overcome the limitation of the short-range wireless communication, the Device 20 of the invention is able to connect wirelessly to a Relay Device 22 that in turn provides the connection to the mobile telephone network 24 for both voice and data traffic. There may be a hardware implemented Device 20, a software implemented Device 20, or both hardware and software-implemented Devices 20.

The Relay Device 22 is normally not connected to the Device 20, but waits for connection attempts from any devices. When a Device 20 moves out of range of the Console 10, the connection attempt will be received by the Relay Device 22. The Device will be able to connect to either a Relay or a Console at any given time, with Consoles being given the priority over Relays. Connection attempt to a Relay will only be successful if no connection to any Consoles is possible. The Relay Device will then create a connection with the Device 20 and act as the Console for that Device which will show a normal connected state instead of being out-of-range. The Relay Device 22 does not connect to the mobile telephone network 24 until an emergency alert is triggered at the Device 20, unless it is generating frequent periodic updates of telehealth data such as output from a motion sensor. Power consumption for the Relay Device is thus minimized.

Figure 2:
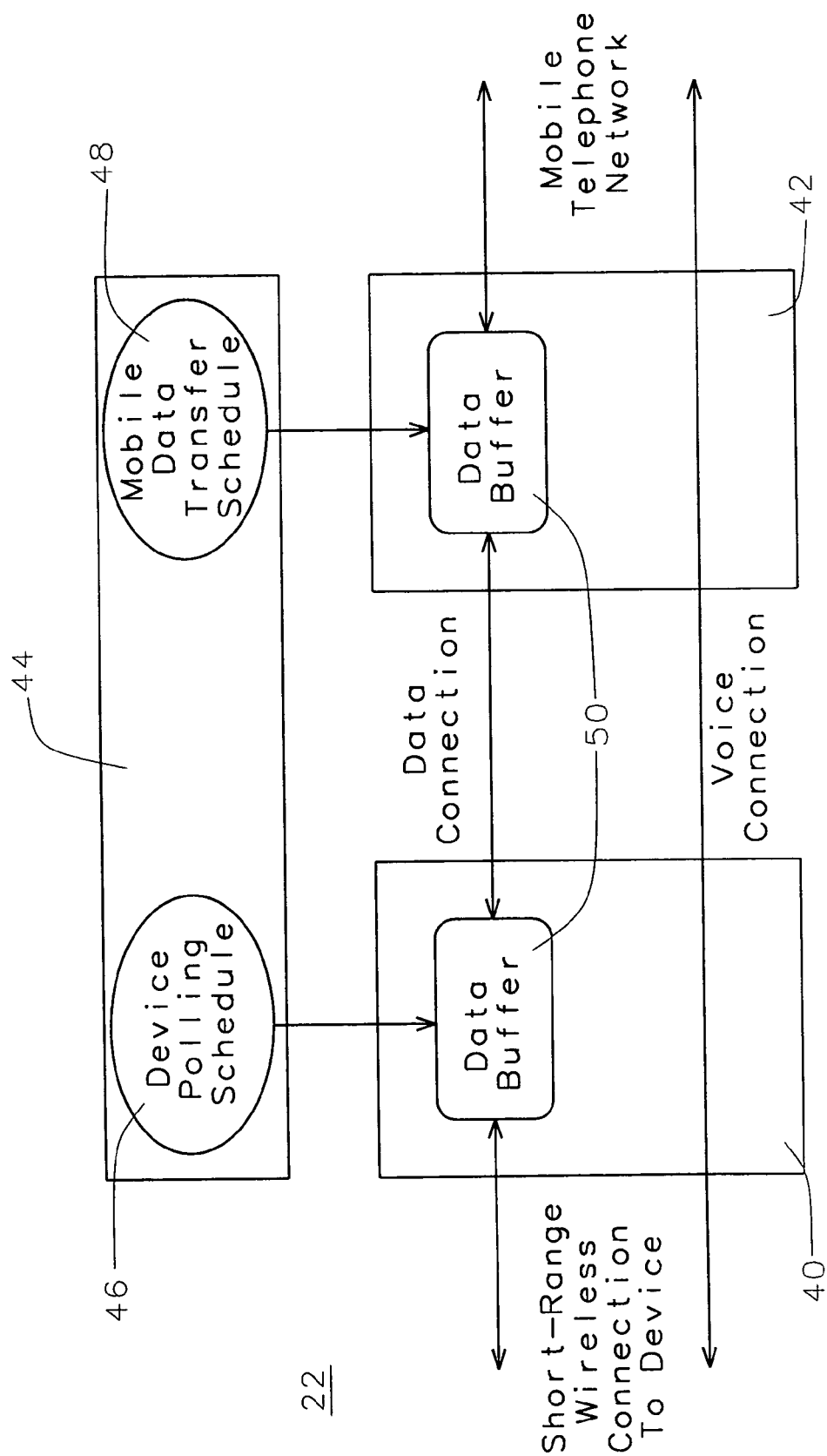
FIG. 2 schematically illustrates relay device implementation of the present invention.

As illustrated in FIG. 2, the Relay Device 22 contains a short-range radio 40 for communicating with Devices, as well as a mobile telephone radio 42 for communicating to the public mobile telephone network. It also contains a power manager 44 that manages how often data is transferred between the Relay and the Device, as well as between the Relay and the mobile telephone network, according to a device polling schedule 46 and the mobile data transfer schedule 48, respectively. These schedules are independent in order to provide optimal control over power consumption and data transfer latency. Data buffers 50 are thus required to provide data flow control. In contrast, a voice connection is functionally just a transparent transfer of voice information between the Device and the mobile telephone network.

The Relay Device is most conveniently implemented as objects habitually carried by a person when that person leaves the residence. One such embodiment is a key chain or key fob, which is carried together with the house keys or car keys. Another embodiment is a credit card-sized module kept inside the user's wallet.

The Device 20 also incorporates a display to show alphanumeric and graphic information, push buttons for user interface to support functions including emergency alert (panic button), motion sensor, two-way voice communications, In-Case-of-Emergency information (ICE), and other peer-to-peer Devices (e.g. light switch, gate reader). It may be implemented as a wearable device such as a wrist-watch, bracelet, pendant, or belt attachment, or the like. The Device may connect to Application Gateways (AG) 14 through the Console 10, via the Internet. It may also connect to third-party servers 16 hosting personal health records (PHR).

Figure 3:
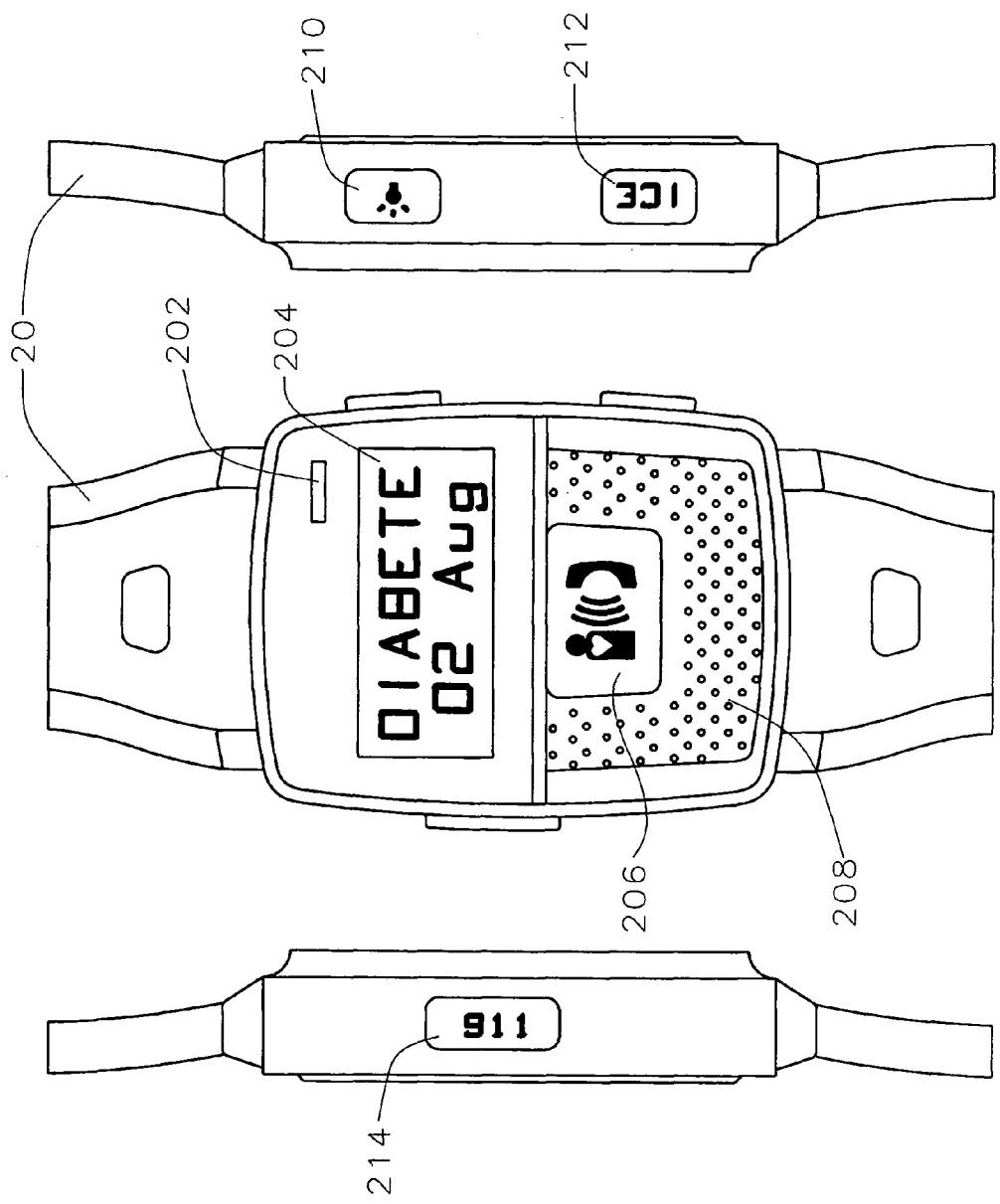
FIG. 3 schematically illustrates a first preferred embodiment of a hardware version of the personal health management device of the invention.
Figure 4:
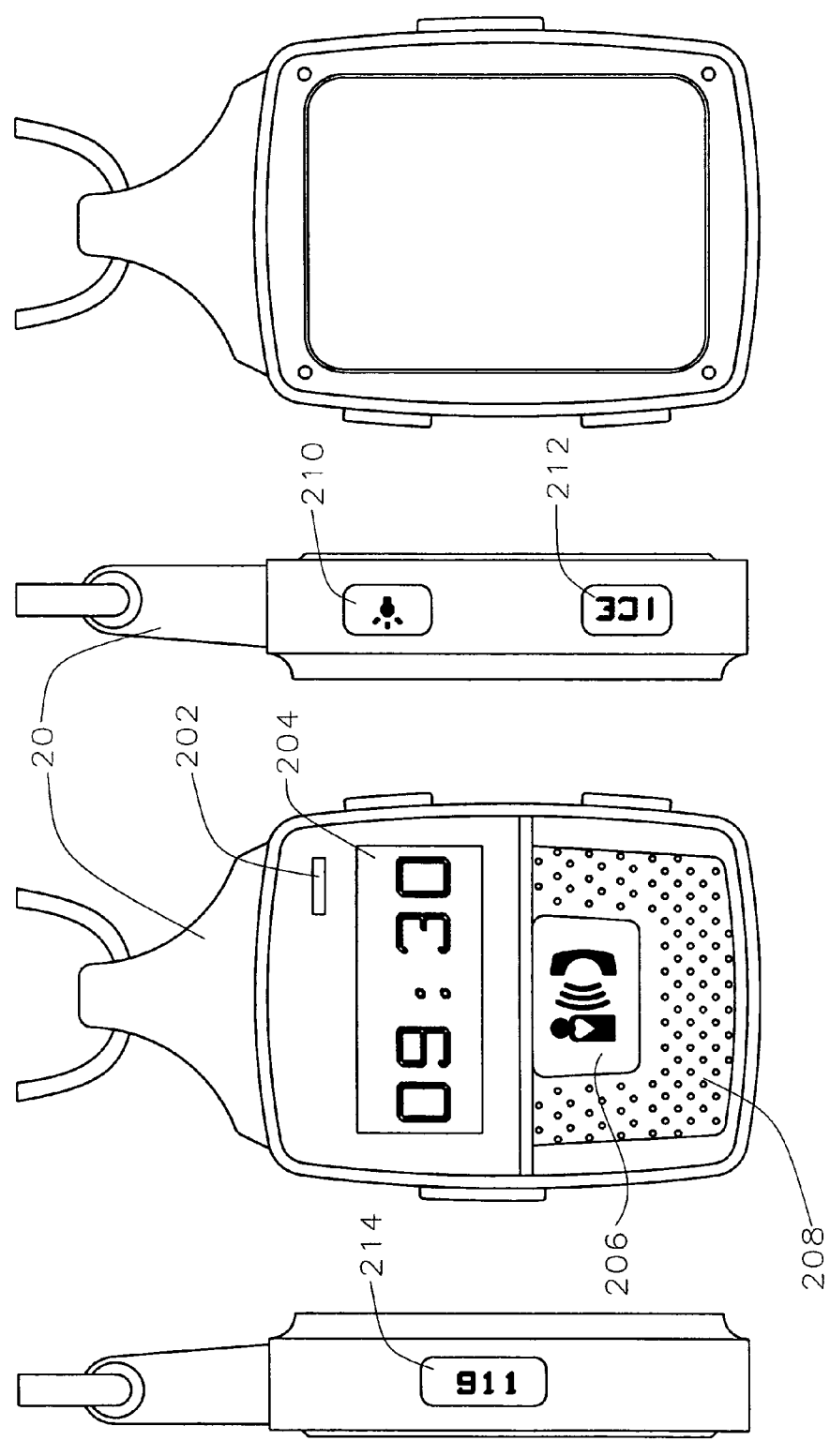
FIG. 4 schematically illustrates a second preferred embodiment of a hardware version of the personal health management device of the invention.

FIGS. 3 and 4 illustrate two preferred embodiments of the invention in which the Device 20 is implemented as a watch (FIG. 3) or a pendant (FIG. 4). It will be understood that the Device 20 may differ from the illustration; that it may be in a different form, such as a belt attachment, or other form, and that the arrangement of the display and buttons, etc., may differ from the arrangements illustrated without departing from the spirit and scope of the invention. FIG. 3 illustrates the device 20 implemented as a watch in front view in the center and two side views. Shown are a display 204 to show alphanumeric and graphic information (including current time), push buttons for user interface to support functions including emergency alert one-touch access to 911 services 214, favorite help button 206 (a one-touch connection to the central console), In-Case-of-Emergency information (ICE) 212, and other peer-to-peer Devices such as a light switch 210. Two-way voice communications are implemented through the microphone 202 and speaker 208. The motion sensor is a chip in the device, so is not illustrated in the drawings.

The favorite help button is used to trigger the automated and sequential calling of one or more telephone numbers pre-configured as the favorite call list at the console. Typical examples of such telephone numbers include those of the user's neighbors, friends or family members. The favorite call list is called one at a time, and depending on the action of each called party, the calling sequence may continue, or it may stop at the current called party. The actions that the called party may take include the pressing of any DTMF keys, thus signaling to the console to stop further calling.

FIG. 4 illustrates the device 20 implemented as a pendant in front view, two side views, and back view. Shown are a display 204 to show alphanumeric and graphic information, push buttons for user interface to support functions including emergency alert one-touch access to 911 services 214, favorite help button 206 (a one-touch connection to the central console), In-Case-of-Emergency information (ICE) 212, and other peer-to-peer Devices such as a light switch 210. Two-way voice communications are implemented through the microphone 202 and speaker 208.

Figure 7:
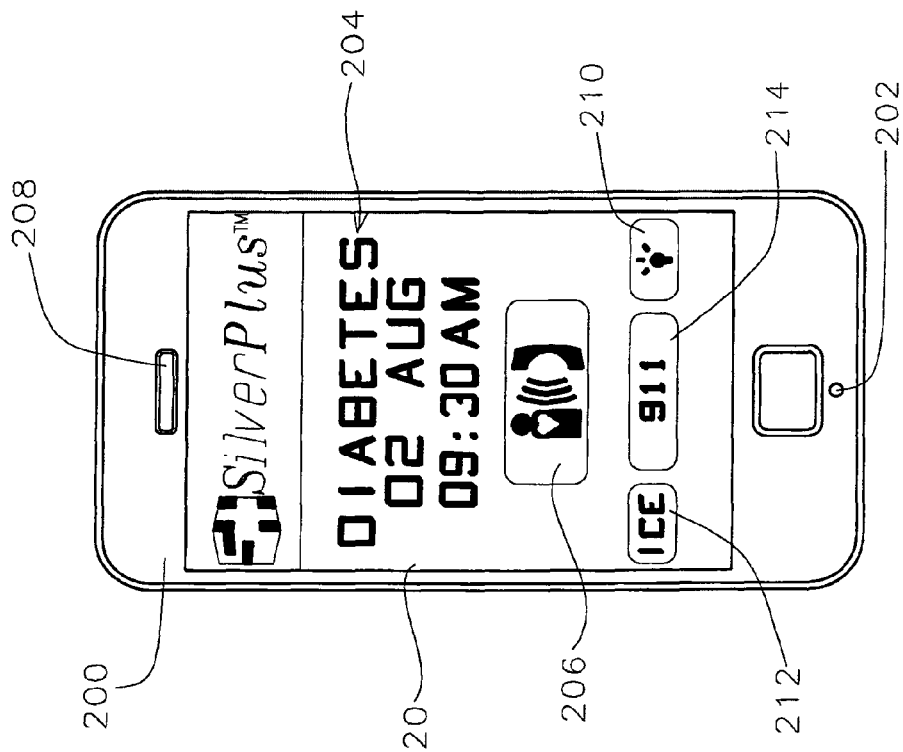
FIG. 7 schematically illustrates a preferred embodiment of a software version of the personal health management device of the invention.

FIG. 7 illustrates a software implemented Device 20. For example, the software implemented device 20 may reside on third party hardware such as a cellular telephone 200. Shown are a display 204 to show alphanumeric and graphic information. touchscreen buttons for user interface to support functions including emergency alert one-touch access to 911 services 214, favorite help button 206 (a one-touch connection to the central console), In-Case-of-Emergency information (ICE) 212, and other peer-to-peer Devices such as a light switch 210. Two-way voice communications are implemented through the microphone 202 and speaker 208 of the cellular telephone or similar hardware device.

Most PERS devices are single-functioned emergency buttons only. Some have time (watch) functions but the lack of a low-power two-way wireless link prohibits any features that require information update from the Console or network to the Device. By having the two-way link, the Device can be reconfigured as new applications are added and thus provide extendable features. For example, a wireless light switch can be associated with the system through the Console 10, and the information is sent to the Device 20 so that the light switch can then be controlled by that particular Device only, for example, using the push button 210 illustrated in FIGS. 3 and 4.

One particularly relevant telehealth data parameter is user motion or activity level, which often is a very good indication of an emergency; for example, when there has not been motion for an extended period of time during the normally active part of the day for a particular user. Typically, personal emergency response system (PERS) devices do not have the ability to report motion data, mostly due to the high current consumption of motion sensors, and also due to the wireless protocol. The personal health management device of the present invention employs a low-power "motion sampling" algorithm and a wireless protocol that sends such data efficiently.

Figure 5:
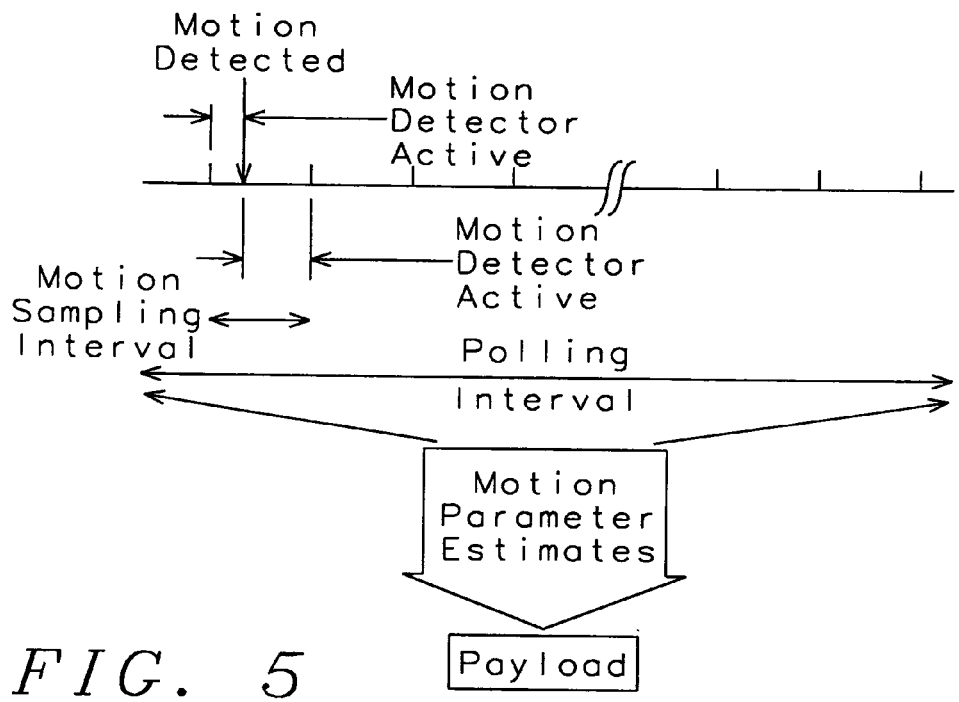
FIG. 5 schematically illustrates the motion detection system of the present invention.

The Device may contain a contact-type motion sensor, and report the presence or absence of motion over predetermined intervals. As shown in FIG. 5, the motion sensor is activated at the beginning of each motion sampling interval, and upon detection of a motion event, will be deactivated until the beginning of the next motion sampling interval. Activation of the motion sensor is performed by the Device based on regular time periods. An efficient implementation is to use the timer available on most common embedded microcontrollers, which allows the microcontrollers to stay in low power sleep mode, and upon timer interrupt will wake up and enable the interrupt that is connected to the motion sensor. The single-bit information for each sampling interval is processed to form payload packets which are transmitted to the Console at predetermined polling intervals equivalent to multiples of the motion sampling intervals. The bit patterns for each polling intervals are used in an algorithm to derive intermediate parameters relating to the activity levels, and the parameters are transmitted to the Console.

The sampling interval determines the time resolution of the motion sensor reports. A shorter interval gives more accurate motion information at the expense of higher power consumption at the Device. For safety monitoring applications a very long sampling interval is sufficient to capture the occurrence of motion over a period in which the user is expected to have moved. For more accurate assessment of activity level, the sampling intervals can be made shorter to capture the amount of motion over different time intervals. For optimal tradeoff between power consumption and time resolution, the sampling interval can be dynamically configured so that sampling intervals are gradually reduced down to a minimum when motion is constantly observed over consecutive sampling intervals, or conversely, gradually increased up to a maximum when there is little motion detected.

Figure 6:
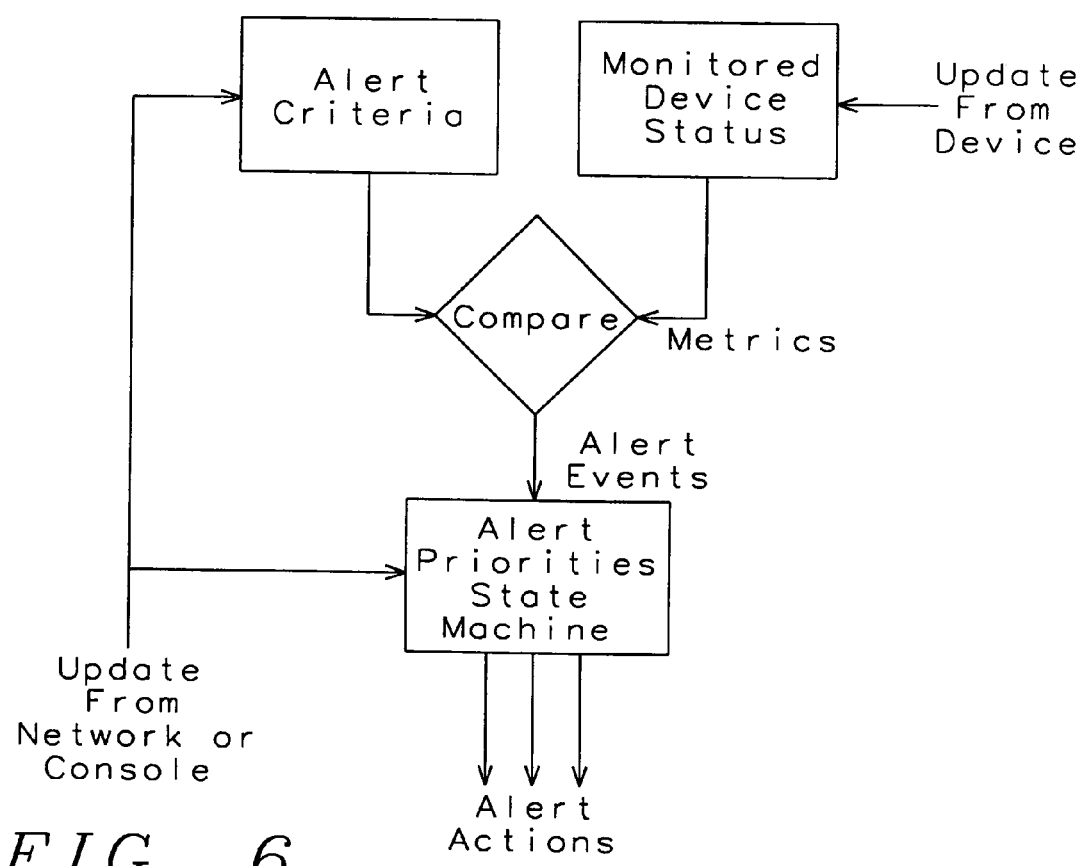
FIG. 6 schematically illustrates the dynamically programmable alert system of the present invention.

The Device can process information provided to it by the Console or the network (including AG and PHR Servers). Such information may be alert criteria which, when combined with status in the Device, may generate alert conditions upon which the Device will then send alert messages to the Console. Alternatively it may only generate local actions such as sounding an audible alarm. The processing of the alert criteria against events, and the subsequent actions, are determined by a dynamically programmable state machine. The actions can be prioritized by the state machine logic which may be updated itself by information provided from the Console. This is illustrated schematically in FIG. 6.

The information that can be received by the Device from the Console relating to alert criteria includes the following:

1) Medication schedule. Upon the condition that actual time coincides with the time for an item in the schedule, the Device will be activated to perform a pre-defined action, such as notifying the user to take medication. For example, the Device may sound an audible alarm and display a message to alert the user to the type and quantity of medication to be taken at that given time. Depending on the user's response to the alert, further actions may be taken by the Device or the system such as notifying the caregiver of failure to respond.

2) Motion sensor alert criteria. Motion parameters and time limits will be defined at the Console and used in the state machine logic as described above. An alert may be sent to the Device if certain criteria are met.

3) PHR parameters alert criteria. Upon certain limits being met for blood pressure, body temperature, heart rate, blood glucose level, weight, and so on, for example, an alert may be sent to the Device.

Other alert criteria may be implemented including appointment scheduling, and other information from third party servers.

Upon an alert generated at the Device, the user may cancel the alert by pressing a button at the Device. The failure of the Device to cancel the alert after a predetermined time interval will result in the Device sending an alert message to the Console or Relay Device, which will in turn notify the caregivers via telephone or Internet.

The Device contains a unique ID that can be configured at production time, or by the AG, Console or Device itself The Device may contain other wired or wireless interfaces to other products with which information may be exchanged and in so doing tagging the information with the unique ID of the Device. For example, vital sign information obtained from diagnostic devices may be sent to the Device via Bluetooth®, and then transmitted by the Device to the Console, adding the unique ID to the information. Diagnostic devices that can be connected to the system as peer-to-peer devices 12 include stand-alone devices such as a weight scale, peak flow meter, glucose meter, blood pressure monitor, portable ECG/EKG device, CPAP machine, and many other devices providing vital sign measurements.

The Device may be implemented in software and reside on other third-party hardware, such as an iPhone, and make use of the inherent motion sensing capability as well as the communication means of such devices to provide the same functions as a dedicated hardware implementation of the Device. The motion sensor may be built into another hardware platform such as an iPhone in the form of a chip.

A software-implemented Device may coexist with a dedicated hardware Device and share the same ID, in which case a handoff mechanism is provided by the Console which will send a data message such as SMS or IP packets to the software-implemented Device via the internet or telephony network, instructing the software-implemented Device to activate or deactivate its motion-reporting function. The handoff may be triggered manually by user actions at the Console, or automatically by events such as the hardware Device being out-of-range for a given time period.

The Device may be in a lock state, in which case the lock screen will display ICE information. Alternatively it may present the user with choices to unlock, or to view the ICE information. This will particularly apply to a Device that is like a mobile telephone.

The Device may store motion data locally, at the rate of 1 bit per sampling period. Given a fixed storage capacity, the motion data may be stored as a running window so that only the most recent data is stored. For historic data outside its storage window, it will also keep a time count from the end of the window to the last motion so that alarm conditions can still be generated based on lack of motion even though not all data is stored.

The Device may store selected PHR information locally and display the information as ICE upon user action such as the press of a button. The filtering of PHR into ICE information is performed by the Console based on a user-programmable mapping table. The mapping table is configured once at the Console and transmitted to the Device, and thereafter any update of the PHR will only result in the corresponding content being transmitted to the Device thus achieving good power efficiency even for frequent updating of PHR.

The implementation of the alert system, using analog telephony, Voice over Internet Protocol (VOIP) over Ethernet or WiFi, and cellular wireless networks, has been described in the co-pending patent application for the Integrated Health Management System. As described in that patent application, an action resulting from an alert comprises sending alerts by email, SMS, fax, or voice calls with pre-recorded voice messages. An application gateway processing acknowledgments of receipt of alerts sends a signal to the console to acknowledge receipt of the alert.

The present invention provides a personal emergency response system with vital signs measurement systems. Health data is provided as part of alert events, and different levels of alert are provided depending on the severity of the events.

While the invention has been particularly shown and described with reference to the preferred embodiments thereof, it will be understood by those skilled in the art that various changes in form and details may be made without departing from the spirit and scope of the invention.

What is claimed is:

1. A personal health management device comprising:
   a radio providing two-way wireless communication with a console unit;
   a display showing alphanumeric and graphic information;
   a user interface to support functions of said personal health management device;
   a communication means coupled to external data and voice networks;
   a wireless communication connection means for receiving vital sign measurements from one or more stand-alone devices and for transmitting same to said console unit;
   a motion sensor detecting the presence or absence of motion in a user of said personal health management device; and
   a relay device maintaining wireless communication with said console unit, wherein said relay device provides connection between said personal health management device and said external data and voice networks when said console unit is out of range, and wherein said console unit provides connection between said personal health management device and said external data and voice networks when said console unit is within range.

2. The device according to claim 1 wherein said personal health management device is implemented in software and resides on third-party hardware wherein said hardware provides said two-way wireless communication, said showing alphanumeric and graphic information, said user interface, said connection to external data and voice networks, and said detecting motion.

3. The device according to claim 1 wherein said showing alphanumeric and graphic information further comprises showing current time.

4. The device according to claim 1 wherein said user interface to support functions of said personal health management device comprises push buttons on said personal health management device.

5. The device according to claim 1 wherein said personal health management device is a wearable device comprising a bracelet, pendant, wrist-watch, or a belt attachment and wherein said relay device is carried on said user's person.

6. The device according to claim 1 wherein said communication means coupled to said external data and voice networks comprises communicating with external data and voice networks by one or more of the following: analog telephony, Voice over Internet Protocol (VOIP) over Ethernet, WiFi, and cellular wireless networks.

7. The device according to claim 1 wherein said detecting the presence or absence of motion in a user comprises:
   providing a motion sampling interval, a polling interval, and alert criteria set at said console unit;
   activating said motion sensor at the beginning of said motion sampling interval;
   deactivating said motion sensor at the end of said motion sampling interval or upon detection of a motion in said user;
   sending motion information from said personal health management device to said console unit indicating motion or no motion for said polling interval; and
   sending an alert from said console unit to said personal health management device based on said motion information and said alert criteria.

8. A system comprising two personal health management devices according to claim 7,
   wherein a first said personal health management device comprises a dedicated hardware device, and a second said personal health management device comprises a software-implemented personal health management device residing on third party hardware, wherein said first and second personal health management devices share a single identification code,
   wherein said console unit provides a handoff mechanism which will send a data message to said software-implemented device, instructing said software-implemented device to activate or deactivate sending motion information to said console unit, and
   wherein said handoff mechanism may be triggered manually by an action of said user at said console unit or automatically by said dedicated hardware device being out-of-range for a given time period.

9. The device according to claim 1 wherein said one or more stand-alone devices comprise a weight scale, peak flow meter, glucose meter, blood pressure monitor, portable ECG/EKG device, or a CPAP machine.

10. A health management system comprising:
- at least one console unit;
- one or more personal health management devices in two-way wireless communication with said console unit wherein said console unit acts as an intelligent gateway through which said one or more personal health management devices may communicate to external data and voice networks, wherein each said personal health management device comprises:
  - a radio providing two-way wireless communication with said console unit;
  - a display showing alphanumeric and graphic information;
  - a user interface to support functions of said personal health management device;
  - communication means coupled to said external data and voice networks; and
  - a motion sensor detecting the presence or absence of motion in a user of said personal health management device;
- a relay device maintaining wireless communication with said console unit, wherein said relay device provides connection between said personal health management device and said external data and voice networks when said console unit is out of range, and wherein said console unit provides connection between said personal health management device and said external data and voice networks when said console unit is within range;
- one or more stand-alone devices in wireless communication with said console unit and with said personal health management device, wherein said one or more stand-alone devices collect personal health data from said user and transmit said personal health data to said personal health management device and wherein said personal health management device transmits said personal health data to said console unit at predetermined polling intervals;
- an application gateway in communication with said at least one console unit wherein said application gateway interfaces with one or more third-party servers; and
- an alert system, wherein an alert can be triggered by an input by said user through said user interface and by pre-set alarm criteria associated with said motion sensing or said collected personal health data or based on a communication received from said one or more third-party servers, and wherein said triggering of an alert causes said console unit to take an action, wherein said console unit's action includes sending the alert to said personal health management device.

11. The system according to claim 10 wherein all components of said personal health management device are implemented in software and reside on third-party hardware.

12. The system according to claim 10 wherein said showing alphanumeric and graphic information further comprises showing current time.

13. The system according to claim 10 wherein said personal health management device is a wearable device comprising a bracelet, pendant, wrist-watch, or a belt attachment supporting said functions of said personal health management device through push buttons on said wearable device and wherein said relay device is carried on said user's person.

14. The system according to claim 10 wherein said user's input comprises pushing a button on said console unit or on one of said personal health management devices.

15. The system according to claim 10 wherein said pre-set alarm criteria comprise analysis by said alert system of communication from one or more of said personal health management devices.

16. The system according to claim 10 wherein said console unit's action comprises placing a telephone call to a public emergency number and, during said telephone call, playing a pre-recorded message including said personal health data transmitted from said personal health management device to said console unit.

17. The system according to claim 16 wherein said console unit's action comprises displaying upon the console unit placing each telephone call the called party's name and telephone number.

18. The system according to claim 16 wherein said personal health data comprises:
- data collected from said one or more stand-alone devices; and
- data stored on said one or more third party servers, wherein said data on said one or more third-party servers is updated from said console unit with said data collected, and wherein said data stored on said one or more third party servers is sent by said console unit along with said pre-recorded message.

19. The system according to claim 10 wherein said console unit's action comprises placing a telephone call to pre-configured telephone numbers sequentially, and, during each said telephone call, playing a pre-recorded message including said personal health data.

20. The system according to claim 10 wherein said console unit's action further comprises sending alert messages by email, SMS, fax, or voice calls to a list of contacts associated with said alert.

21. The system according to claim 20 wherein said application gateway sends a signal to said console unit to acknowledge receipt of said alert messages.

22. The system according to claim 10, wherein said detecting the presence or absence of motion in said user comprises:
- providing a motion. sampling interval, a polling interval, and said pre-set alarm criteria set at said console unit;
- activating said motion sensor at the beginning of said motion sampling interval;
- deactivating said motion sensor at the end of said motion sampling interval or upon detection of a motion in said user;
- sending motion information from said personal health management device to said console unit indicating motion or no motion for said motion sampling interval; and
- sending an alert from said console unit to said personal health management device based on said motion information and said pre-set alarm criteria.

23. The system according to claim 10 wherein:
- medication prescription information is able to be provided by said third party server wherein said medication prescription information comprises a medication schedule;
- said medication prescription information is able to be sent by said third party server to said console unit through said application gateway;
- said console unit sends alert messages to said personal health management device according to said medication schedule; and
- said personal health management device generates audio or visual alerts autonomously using information from said medication schedule.

24. The system according to claim 10 wherein said one or more stand-alone devices comprise a weight scale, peak flow meter, glucose meter, blood pressure monitor, portable ECG/EKG device, or a CPAP machine.

25. A watch, having health-related functions, and a relay device; said watch comprising:
- a user interface to support said health-related functions of said watch, wherein said health-related functions comprise: a personal emergency alert function, two-way voice communication, in-case-of-emergency (ICE) information storage and communication capability, event reminder capability, motion sensor data collection and transmission, and home control activation functions controlling aspects of a home;
- a radio providing two-way wireless communication with a console unit;
- a display showing alphanumeric and graphic information including current time;
- a communication means coupled to external data and voice networks; and
- a wireless communication connection means for receiving vital sign measurements from one or more stand-alone devices and for transmitting same to said console unit; and
- said relay device maintaining wireless communication with said console unit, wherein said relay device provides connection between said watch and said external data and voice networks when said console unit is out of range, and wherein said console unit provides connection between said watch and said external data and voice networks when said console unit is within range.

26. The watch according to claim 25 wherein said user interface to support said health-related functions of said watch comprises push buttons on said watch.

27. The watch according to claim 25 wherein said communication means coupled to said external data and voice networks comprises communicating with external data and voice networks by one or more of the following: analog telephony, Voice over Internet Protocol (VOIP) over Ethernet, WiFi, and cellular wireless networks.

28. The watch according to claim 25 wherein said motion sensor data collection and transmission comprises:
- providing a motion sensor on said watch;
- providing a motion sampling interval, a polling interval, and pre-set alarm criteria set at said console unit;
- activating said motion sensor at the beginning of said motion sampling interval;
- deactivating said motion sensor at the end of said motion sampling interval or upon detection of a motion in a user;
- sending motion information from said watch to said console unit indicating motion or no motion for each polling interval; and
- sending an alert from said console unit to said watch based on said motion information and on said pre-set alarm criteria.

29. The watch according to claim 25 wherein said one or more stand-alone devices comprise a weight scale, peak flow meter, glucose meter, blood pressure monitor, portable ECG/EKG device, or a CPAP machine.

30. A method for health management of a user comprising:
- providing a first personal health management device, showing alphanumeric and graphic information, said first personal health management device in two-way wireless communication with a console unit;
- providing one or more stand-alone devices in wireless communication with said console unit and with said first personal health management device, wherein said one or more stand-alone devices collect personal health data from said user and transmit said personal health data to said first personal health management device;
- transmitting said personal health data to said console unit;
- collecting additional data from said first personal health management device and storing said additional data at said console unit;
- uploading said personal health data and said additional data to an application gateway in communication with said console unit wherein said application gateway sends said personal health data and said additional data to one or more third-party servers;
- maintaining wireless communication between said first personal health management device and said console unit by means of a relay device, wherein said relay device provides connection between said first personal health management device and external data and voice networks when said console unit is out of range, and wherein said console unit provides connection between said first personal health management device and said external data and voice networks when said console unit is in range; and
- providing an alert system, wherein an alert can be triggered by an input by said user through a user interface to said first personal health management device and by pre-set alarm criteria associated with said collected personal health data or with values of collected said additional data or based on a communication received from said one or more third-party servers, and wherein said triggering of an alert causes said console unit to take an action.

31. The method according to claim 30 wherein said first personal health management device is implemented in software and resides on third-party hardware wherein said hardware provides said two-way wireless communication, said showing alphanumeric and graphic information, said user interface, and said connection to said external data and voice networks.

32. The method according to claim 31 further comprising connecting said console unit to said external data and voice networks by one or more of the following:
analog telephony, Voice over Internet Protocol (VOIP) over Ethernet, WiFi, and cellular wireless networks.

33. The method according to claim 31 further comprising a second personal health management device which comprises a dedicated hardware device sharing the same identification code as said first personal health management device, wherein said console unit provides a handoff mechanism which will send a data message to said software-implemented device, instructing said software-implemented device to activate or deactivate sending motion information to said console unit wherein said handoff mechanism may be triggered manually by an action of said user at said console unit or automatically by said dedicated hardware device being out-of-range for a given time period.

34. The method according to claim 30 wherein said two-way wireless communication with a console unit comprises a radio residing in said first personal health management device and wherein said relay device is carried on said user's person.

35. The method according to claim 30 wherein said user interface comprises push buttons on said first personal health management device.

36. The method according to claim 30 wherein said first personal health management device is a wearable device comprising a bracelet, pendant, wrist-watch, or a belt attachment.

37. The method according to claim 30 further comprising:
providing a motion sensor on said first personal health management device;
setting a motion sampling interval, a polling interval, and second pre-set alarm criteria at said console unit;
activating said motion sensor at the beginning of said motion sampling interval;
deactivating said motion sensor at the end of said motion sampling interval or upon detection of a motion in said user;
sending motion information from said first personal health management device to said console unit indicating motion or no motion for each polling interval; and
sending an alert from said console unit to said first personal health management device based on said motion information and said second pre-set alarm criteria.

38. The method according to claim 30 wherein said one or more stand-alone devices comprise a weight scale, peak flow meter, glucose meter, blood pressure monitor, portable ECG/EKG device, or a CPAP machine.

* * * * *